United States Patent [19]

Delwiche et al.

[11] Patent Number: 4,743,445

[45] Date of Patent: May 10, 1988

[54] METHOD FOR TREATMENT OF ESSENTIAL (HEMORRHAGIC) THROMBOCYTHEMIA

[75] Inventors: Francis Delwiche, Genval; Jocelyn Flament-Grivegnee; Diamond Gangji, both of Brussels; Rita Monsieur, Kester; Pierre Stryckmans, Meise; Thierry Velu, Waterloo; Joseph Wybran, Brussels, all of Belgium

[73] Assignee: Boehringer Ingelheim International GmbH, Fed. Rep. of Germany

[21] Appl. No.: 758,729

[22] Filed: Jul. 25, 1985

[51] Int. Cl.$^4$ .............................................. A61K 45/02
[52] U.S. Cl. ...................................... 424/85; 435/811
[58] Field of Search ...................... 424/85; 260/112 R; 435/68

[56] References Cited

PUBLICATIONS

Chemical Abstracts, vol. 102, p. 469, Abstract No. 219435d, 1985.

Urushiyami et al.; *Igaku no Ayumi* 131(11/12): 739-740 (1984).
Talpaz et al., Ann. Int. Med. 99: 787-792 (1983).
Cantell et al., J. gen. Virol. 39:541-543 (1978).
Zor et al., J. gen. Virol. 63:359-363 (1982).
Baracos et al., N. Eng. J. Med., vol. 308: No. 10, pp. 553-558 (1983).
Harrison's *Principles of Internal Medicine*, McGraw-Hill, N.Y., p. 1898 (1983).
Velu et al., Blood 64(5), Supp. 1, 176a Abstract No. 6116 (Nov. 1984).

*Primary Examiner*—Blondel Hazel
*Attorney, Agent, or Firm*—Saidman, Sterne, Kessler & Goldstein

[57] ABSTRACT

A method for the treatment of essential thrombocythemia, said method comprising the administration of alpha-type interferons in an amount and for a period of time sufficient to reduce the platelet count to physiologically acceptable levels.

9 Claims, No Drawings

METHOD FOR TREATMENT OF ESSENTIAL (HEMORRHAGIC) THROMBOCYTHEMIA

BACKGROUND OF THE INVENTION

1. Field of the Invention

The present invention is directed to the discovery that a certain family of interferons, the alpha-type interferons, demonstrate a previously unrecognized utility in the treatment of essential (hemorrhagic) thrombocythemia. The treatment, comprising administration of effective amounts of alpha-type interferons, substantially reduces the risk of thrombosis in patients suffering from the disease.

2. Brief Description of the Background Art

Interferon is a potent antiviral glycoprotein released by animal cells following viral infection and also after treatment of such cells with certain nonviral inducers. This constitutes one of the major defense mechanisms against viral infections in mammals, including humans. In addition to its antiviral function, interferon has been found to have immunoregulatory activities, to affect various cellular functions including cell division, and to have value as an anti-cancer drug.

Much research and developmental effort has been applied to the large scale production of human interferon. Interferons are used to treat virus diseases and also to treat tumors of viral and/or non-viral origin (see, for example, Powledge, *Bio/Technology*, "Interferon On Trial," pp. 215–222, March 1983).

Human interferons (HuIFN) have been classified into three groups: alpha-interferon (HuIFN-alpha), beta-interferon (HuIFN-beta) and gamma-interferon (HuIFN-gamma). HuIFN-alpha, also known as leukocyte interferon, is produced in human leukocyte cells and together with minor amounts of HuIFN-beta, also called fibroblast interferon, in lymphoblastoid cells. HuIFN-gamma is produced in cultures of lymphocytes, particularly in cultures enriched for T-cells.

Only one type each of HuIFN-beta and HuIFN-gamma has been found in the human organism (Ohno, S. et al., *Proc. Natl. Acad. Sci.*, 76: 5305–5309 (1981); Gray et al., *Nature*, 295: 503–508 (1982); Taya et al., *EMBO Journal*, 1/8: 953–958 (1982)). On the other hand, various sub-types of HuIFN-alpha are known from the literature (*Phil. Trans. R. Soc., London*, 299: 7–28 (1982); and British Patent Application No. 2,037,296A). The various forms of HuIFN-alpha, hereinafter alpha-type interferons, appear to differ from each other structurally and physiologically. However, they all appear to be about 166 amino acids long with the mature interferons differing from one another by a divergence of up to about 25% of the amino acid sequences. The interferons currently used therapeutically in human medicine are obtained from human leukocytes, from reproducible human fibroblasts, and human lymphoblastoid cell cultures and from microorganisms. The human genes coding for interferon are incorporated in various microorganisms, including *E. coli*. The production of alpha-type interferon using recombinant DNA technology is described in European Patent Application No. 0 032 134, published Aug. 15, 1984, and European Patent Application No. 0 043 980, published Jan. 20, 1982, both incorporated by reference herein.

Thrombocytosis is a term used to describe a temporary elevation of platelet count above $400 \times 10^3/\mathrm{ul}$ which may occur after severe hemorrhage, surgery, or splenectomy. The condition exists as well in cases of iron deficiency. Thrombocytosis may also occur in chronic inflammatory disorders and following recovery from acute infection. Malignant diseases such as carcinoma and Hodgkin's disease may also be associated with thrombocytosis. See Harrison's *Principles of Internal Medicine*, Tenth Edition, McGraw-Hill, Inc., p. 1898 (1983).

Thrombocythemia refers to a sustained elevation of platelet count, usually above about $800 \times 10^3/\mathrm{ul}$. This condition, generally considered to be a myeloproliferative disorder, usually manifests itself with the spleen sufficiently enlarged to be detected by abdominal palpation. Thrombocythemia may occur as a part of polycythemia vera, chronic myelogenous leukemia, or myelosclerosis. It may also occur alone, in which case it is termed essential (hemorrhagic) thrombocythemia. Patients with essential thrmobocythemia frequently manifest spontaneous bleeding as well as venous and arterial thrombosis. Platelet function studies such as aggregation and platelet factor III activity are often abnormal. See Harrison's, supra, p. 1898.

Prior art treatment for essential thrombocythemia involves therapy to decrease the autonomous growth of megakaryocyte and the resulting excessive platelet production. Suitable reagents for this type of therapy includes $^{32}P$, busulfan, or another alkylating agent. See Harrison's, supra, p. 1898. Where thrombosis develops, heparin therapy is required. Aspirin and dipyridamole have been successfully used in peventing thrombosis.

Talpaz et al., *Ann. Intern. Med.*, 99: 789–792 (1983), has described the use of HuIFN-alpha prepared according to Cantrell et al. (*J. Gen. Virol.*, 39: 541–543 (1973)) for adjunct therapy in the treatment of thrombocytosis in patients with chronic myelogenic leukemia. The patients were simultaneously treated by chemotherapy with cytostatics, e.g. with cyclophosphamide, cytarabine, vincristine, hydroxyurea, 6-mercapto-purine, busulfan and mixtures thereof. However, this methodology resulted in serious side effects such as fever, weight loss, neuromuscular pains, and the like. Similar deleterious side effects are reported at *J. Gen. Virol.*, 63: 354–363 (1982) and *N. Eng. J. Med.*, 308: 553–558 (1983).

Further, during treatment with cytostatics or mixtures thereof, the number of white blood corpuscles and blood platelets (thrombocytes) is generally always reduced. Accordingly, the dosage of cytostatics used must be selected so that the resulting side effects, e.g., the lowering of resistance to infections and anemia, remain tolerable in relation to the objective of the therapy.

However, in spite of the many advances reported in the use of HuINF-alpha for the treatment of a variety of diseases of tumor and viral origin, and even in the face of the Talpaz et al. (supra) disclosure relaing to the treatment of chronic myelogenic leukemia and the thrombocytosis resulting therefrom by a combination of HuIFN-alpha and various cytostatics, a need has continued to exist for a safe and effective treatment for thrombocythemia which avoids the undesirable side effects of chemotherapy with cytostatics.

SUMMARY OF THE INVENTION

In accordance with this invention, the inventors have discovered a method for safely and effectively treating essential thrombocythemia, that is thrombocythemia which is unassociated with polycythemia vera, chronic myleogenous leukemia, or myelosclerosis. The method of the present invention comprises administering alpha-type interferons, in an amount effective to reduce the platelet count to a range of about 300–600×10³/ul.

DESCRIPTION OF THE PREFERRED EMBODIMENTS

As described above, the method of the invention comprises the administration of alpha-type interferons, in an effective amount, to human patients suffering from essential thrombocythemia. For the purpose of this invention, the term "alpha-type interferon" is meant to include any and all of the human interferons which have been classified as the alpha-type. Accordingly, the term includes those interferons produced in human leukocyte cells as well as those obtained from reproducible human fibroblasts and human lymphoblastoid cell cultures. The term includes interferon in both its glycosylated form and in its non-glycosylated form. This non-glycosylated form has been reported by Stewart, W. E. II et al. in "Effect of Glycosylation Inhibitors on the Production and Properties of Human Leukocyte Interferon," *Virology*, 97: 473–476 (1979). Further included are the several different forms reported in British Patent Application No. 2,037,296A, these forms differing structurally and physiologically.

Also included within the term are those alpha-type interferons which are produced by genetically engineered microorganisms. Typical recombinant human interferons of the alpha type are disclosed in published European Patent Application Nos. EP-A-95702 and EP-A-115613. Included as well are interferons of the alpha type as reported by Goeddel, D. V. et al., *Nature*, 287: 412 (1980).

Further included are hybrid molecules of interferon, typically molecules which are hybrids of interferon-alpha-1 and interferon-alpha-2, disclosed in published European Patent Application No. 0 032 134 and incorporated by reference herein.

A preferred recombinant alpha-type interferon for the method of this invention is HuIFN-alpha-2(Arg), disclosed in the above-mentioned EP-A-95702 and EP-A-115613 European Patent Applications. HuIFN-alpha-2(Arg) may be produced using techniques known to the art by the fermentation of *E. coli* transformed with plasmid 1F7, and IFN-alpha-type clone which was deposited in microorganism DSM-2362 on May 17, 1982 at the Deutsche Sammlung von Mikro Organismen, Grisebachstrasse 8, 3400 Gottingen G. This deposit is available to the public according to the Budapest Convention.

The DNA sequence of the IFN-alpha-type clone (1F7) was analyzed according to the dideoxy-method (see Messing et al. in *Nuc. Acid. Res.*, 9, 309 (1982) and Gardner, R. C. et al. in *Nuc. Acid. Res.*, 9, 2871 (1981). The following partial DNA sequence for positions 120 to 327 was found:

```
... CCTGGCACAGATGAGGAGAATCTCTCTTTTCT
CCTGCTTGAAGGACAGACGTGACTTTGGATTTCCCC
AGGAGGAGTTTGGCAACCAGTTCCAAAAGGCTGAAA
CCATCCCTGTCCTCCATGAGATGATCCAGCAGATCT
TCAATCTCTTCAGCACAAAGGACTCATCTGCTGCTT
GGGATGAGACCCTCCTAGACAAATTCTA ...
```

A comparison with the known sequence for IFN-alpha-A type (see D. V. Goeddel et al. in *Nature*, 290, 20 (1981) demonstrates that the DNA for the 1F7 plasmid differs from that reported by Goeddel et al. in the presence of the nucleotide G at positions 137 and 170 in the 1F7 plasmid as compared to the nucleotide A for the sequence reported by Goeddel et al.

Thus, from the sequence of the known mature IFN-alpha-A, the sequence derived from clone 1F7 and the universal genetic code, the protein structure of the mature interferon obtained from clone 1F7, that interferon known in this application as HuIFN-alpha-2(Arg), is as follows:

--- cys—asp—leu—pro—gln—thr—his—ser—leu—
gly—ser—arg—arg—thr—leu—met—leu—leu—
ala—gln—met—arg—arg—ile—ser—leu—phe—
ser—cys—leu—lys—asp—arg—arg—asp—phe—
gly—phe—pro—gln—glu—glu—phe—gly—asn—
gln—phe—gln—lys—ala—glu—thr—ile—pro—
val—leu—his—glu—met—ile—gln—gln—ile—
phe—asn—leu—phe—ser—thr—lys—asp—ser—
ser—ala—ala—trp—asp—glu—thr—leu—leu—
asp—lys—phe—tyr—thr—glu—leu—tyr—gln—
gln—leu—asn—asp—leu—glu—ala—cys—val—
ile—gln—gly—val—gly—val—thr—glu—thr—
pro—leu—met—lys—glu—asp—ser—ile—leu—
ala—val—arg—lys—tyr—phe—gln—arg—ile—
thr—leu—tyr—leu—lys—glu—lys—lys—tyr—
ser—pro—cys—ala—trp—glu—val—val—ala—
ala—glu—ile—met—arg—ser—phe—ser—leu—
ser—thr—asn—leu—gln—glu—ser—leu—arg—
ser—lys—glu.

---

The method of this invetion includes treatment of all diseases which are characterized as essential thrombocythemia. By the term "essential thrombocythemia" is meant to include thrombocythemia as characterized by a sustained elevation of platelet count, typically above 800×10³ platelets/ul, which occurs as a result of unknown etiology, i.e. that which does not result as a part of diseases such as polycythemia vera, chronic myelogenous leukemia, or myelosclerosis. As is known from the literature, patients with essential thrombocythemia frequently manifest spontaneous bleeding as well as venous and arterial thrombosis (see Harrison's, supra). Thus, a typical patient suffering from a pathological increase in thrombocytes resulting from essential thrombocythemia incurs a high risk of thrombosis with all its consequences: embolisms, cerebral blood flow disorders, neurological disorders, and the like. By the method of this invention, the risk of thrombosis is substantially reduced.

The method of this invention, administering alpha-type interferons, includes administration in all manner as is conventional and known to the art, including varying dosage regimes and various modes of administration. Typical interferon therapy is disclosed by Stewart, W. E. et al., (II) in *The Interferon System*, Springer-Verlag, pp. 305–321 (1979), incorporated by reference herein. Typically, interferon may be administered orally, by inoculation, intravenous, intramuscular, intranasal, intradermal, and subcutaneous, and in the form of eye drops, ointments, and sprays. It may be administered 1–3 times daily in dosages of 10⁴ to 10⁷ units per dose. The extent of therapy depends upon the patient and the condition being treated. The most effective therapy for a given patient must, of course, be determined by the attending physician who will consider such well-known factors as the course of the disease, previous therapy, and the patient's response to interferon in selecting a mode of administration and dosage regime.

The preferred mode of administration for the invention method is parenteral administration, preferably by intramuscular route. A typical dosage is in the range of about $5-10 \times 10^6$ IU/day.

In aqueous solution, recombinant human interferon-alpha-2(Arg), also designated rHuIFN-alpha-2(Arg), may be stored for only a limited period without loss of activity. Accordingly, various methods are commonly used to stabilize the interferon. Typical methods of stabilization comprise, both individually and/or in combination, addition of a stabilizer, lyophilization, and freeze-drying from a solution adjusted to a pH which promotes stability.

In the latter instance, the interferon may be reconstituted with solvent and pH and buffer capacity which will bring the solution to a neutral pH for use.

Typically, the solutions for parenteral administration are isoosmotic and isohydric with blood and lymphatic fluid. The following are typical formulations suitable for parenteral administration:

Formulation 1
rHuIFN-alpha-2(Arg): $5 \times 10^6$ IU
isotonic phosphate buffer pH 7: q.s.
human serum albumin: 20.0 mg
water for injection: 1.0 ml Formulation 2
rHuIFN-alpha-2(Arg): $5 \times 10^6$ IU
isotonic phosphate buffer pH 7: q.s.
polyoxyethylene sorbitan monolaurate: 1.0 mg
water for injection: 1.0 ml Formulation 3
rHuIFN-alpha-2(Arg): $5 \times 10^6$ IU
isotonic acetate buffer pH 4: q.s.
human serum albumin: 2.0 mg/ml
water for injection: 1.0 ml Having now generally described the invention, the same will be better understood by reference to the following examples, which are not intended to be limiting unless otherwise stated.

EXAMPLE 1

Four patients meeting the criteria for the diagnosis of essential thrombocythemia were given intramuscular injections of $5 \times 10^6$ IU/per day of rHuIFN-alpha-2(Arg) for 30 days. Every patient had a previous history of cerebrovascular thrombosis. After 15 days, the dose was doubled if the results of the treatment were insufficient. After 30 days, the same dosage was given twice a week as a maintenance dose.

The following table shows that in all the patients the number of thrombocytes returned to normal, except in patient number 4, who was treated with only 24 doses of rHuIFN-alpha-2(Arg):

TABLE 1

| Patient (Age) | Number of Platelets $\times 10^3$/ul at | | | Days to 50% Platelet Reduction |
|---|---|---|---|---|
| | Start of Therapy | Post Therapy Reduction | Maintenance Dose (after 45 days) | |
| 1 (69) | 998 | 301 | 714 | 21 |
| 2 (59) | 935 | 400 | 442 | 21 |
| 3 (77) | 946 | 310 | 580 | 20 |
| 4 (60) | 1544 | 546 | 595 | 29 |
| mean ± SEM | 1106 ± 147 | 583 ± 56 | | 23 ± 2 |

It is particularly worth noting that during the treatment with rHuIFN-alpha-2(Arg) only slight side effects such as fever and fatigue were experienced. At the same time, on average, the number of white blood cells decreased from $12.6 \pm 2.4$ to only $5.7 \pm 1.0 \times 10^3$/ul and the number of red blood cells was reduced from $5.0 \pm 0.3 \times 10^6$ to only $4.0 \pm \times 10^6$/ul during the therapy; therefore in this dosage in these patients rHuIFN-alpha-2(Arg) obviously did not bring about a depression in the white and red blood cell profile to below physiological threshold values.

Having now fully described this invention, it will be appreciated by those of skill in the art that many modifications and variations exist which do not affect or change the scope thereof.

What is claimed as new and desired to be covered by Letters Patent is:

1. A method for treating essential thrombocythemia, said method comprising administering an effective amount of human alpha-type interferon to a human having essential thrombocythemia.

2. The method of claim 1 wherein said human alpha-type interferon is HuIFN-alpha-2(Arg).

3. The method of claim 1 wherein said human alpha-type interferon is administered parenterally.

4. The method of claim 3 wherein said human alpha-type interferon is administered intravenously, intramuscularly, or subcutaneously.

5. The method of claim 3 wherein said human alpha-type interferon is administered as a solution of said alpha-type interferon in a physiologically acceptable carrier.

6. The method of claim 1 wherein said human alpha-type interferon is administered for a time and in an amount sufficient to reduce the number of thrombocytes to a physiologically acceptable level.

7. The method of claim 6 wherein said physiologically acceptable level is in the range of 300 to $600 \times 10^3$ platelets/ul of peripheral blood.

8. The method of claim 1 wherein said human alpha-type interferon is administered in an amount ranging from about $5-10 \times 10^6$ IU/day.

9. The method of claim 8 wherein the dose of said human alpha-type interferon administered is doubled after 15 days.

* * * * *